(12) United States Patent
Karbaum et al.

(10) Patent No.: US 10,472,431 B2
(45) Date of Patent: Nov. 12, 2019

(54) METAL COMPLEX COMPRISING AMIDINE AND SUBSTITUTED CYCLOPENTADIENYL LIGANDS

(71) Applicant: ARLANXEO NETHERLANDS B.V., Geleen (NL)

(72) Inventors: Peter Karbaum, Bonn (DE); Richard Thomas William Scott, Selkirkshire (GB); John Van De Moosdijk, Heerlen (NL)

(73) Assignee: ARLANXEO NETHERLANDS B.V. (NL)

( * ) Notice: Subject to any disclaimer, the term of this patent is extended or adjusted under 35 U.S.C. 154(b) by 0 days.

(21) Appl. No.: 15/511,358

(22) PCT Filed: Sep. 8, 2015

(86) PCT No.: PCT/EP2015/070498
§ 371 (c)(1),
(2) Date: Mar. 15, 2017

(87) PCT Pub. No.: WO2016/041818
PCT Pub. Date: Mar. 24, 2016

(65) Prior Publication Data
US 2017/0240663 A1    Aug. 24, 2017

(30) Foreign Application Priority Data
Sep. 18, 2014   (EP) .................................... 14185359

(51) Int. Cl.
| | |
|---|---|
| *C07F 17/00* | (2006.01) |
| *C08F 4/6592* | (2006.01) |
| *C08F 10/02* | (2006.01) |
| *C08F 210/18* | (2006.01) |
| *C07F 7/28* | (2006.01) |
| *C08F 4/659* | (2006.01) |

(52) U.S. Cl.
CPC ................ *C08F 10/02* (2013.01); *C07F 7/28* (2013.01); *C07F 17/00* (2013.01); *C08F 4/6592* (2013.01); *C08F 210/18* (2013.01); *C08F 4/65908* (2013.01); *C08F 4/65912* (2013.01); *C08F 2420/04* (2013.01)

(58) Field of Classification Search
CPC .............................. C07F 17/00; C08F 4/6592
See application file for complete search history.

(56) References Cited

U.S. PATENT DOCUMENTS

| | | |
|---|---|---|
| 7,956,140 B2 | 6/2011 | Ijpeij et al. |
| 8,957,171 B2 | 2/2015 | Van Doremaele et al. |
| 2013/0066028 A1 | 3/2013 | Van Doremaele et al. |

FOREIGN PATENT DOCUMENTS

| | | |
|---|---|---|
| JP | 2004143434 A2 | 5/2004 |
| JP | 2013055371 A2 | 8/2013 |

OTHER PUBLICATIONS

Chen, E. Y-X, et al., "Cocatalysts for Metal-Catalyzed Olefin Polymerization: Activators, Activation Processes, and Structure-Activity Relationships", Chem. Rev. 2000, 100, American Chemical Society, pp. 1391-1434.
Miyazawa, Akira et al., "Cis-Specific Living Polymerization of 1,3-Butadiene Catalyzed by Alkyl and Alkylsilyl Substituted Cyclopentadienyltitanium Trichlorides with MAO", Macromolecules 2000, 33, American Chemical Society, pp. 2796-2800.
Zhang, Jie et al., "Synthesis and structures of titanium and yttrium complexes with N, N1-tetramethylguanidinate ligands: different reactivity of the M—N bonds toward phenyl isocyanate", Dalton Transactions: [6015A], RSC Publishing, Cambridge, GB, No. 10, Jan. 1, 2009, pp. 1806-1811.
European Search Report from European Application No. 14185359, dated Feb. 19, 2015, two pages.

*Primary Examiner* — Caixia Lu
(74) *Attorney, Agent, or Firm* — Cohen & Grigsby, P.C.

(57) ABSTRACT

A metal complex of the formula (1) $CyLMZ_p(A)_n$ (1), wherein M is a group 4 metal Z is an anionic ligand, p is number of 1 to 2, preferably 2, Cy is a cyclopentadienyl-type ligand substituted with at least one aliphatic $C_3$-$C_{20}$ hydrocarbyl group, which is bonded to the cyclopentadienyl-type ligand, in particular to its cyclopentadienyl ring, via a secondary, a tertiary or quaternary carbon atom and, L is an amidinate ligand of the formula (2), wherein the amidine-containing ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom and A is a neutral Lewis base ligand selected from the list consisting of ether, thioether, amine, tertiary phosphane, imine, nitrile and isonitrile, wherein the number of said metal ligands "n" is in the range of 0 to the amount that specifies the 18-electron rule.

(2)

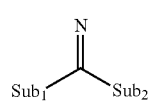

8 Claims, No Drawings

METAL COMPLEX COMPRISING AMIDINE AND SUBSTITUTED CYCLOPENTADIENYL LIGANDS

The present invention relates to a metal complex comprising cyclopentadienyl and amidine ligands substituted with at least one aliphatic $C_3$-$C_{20}$ hydrocarbyl group, which is bonded to the cyclopentadienyl-type ligand via a secondary, a tertiary or quaternary carbon atom, a catalyst system containing said metal complex and a process for manufacturing polymers wherein said metal complex or catalyst system is used.

A process for the polymerization of at least one olefin having 2 to 8 carbon atoms in the presence of a polymerization catalyst component comprising an amidine ligand, an activator, and optionally a scavenger is known from WO2005090418. WO2005090418 discloses a process for the copolymerization of ethylene and at least one additional alpha olefin having from 3 to 8 carbon atoms. Characterized in that said process is a catalyst system for olefin polymerization comprising an organometallic complex of a group 4 metal comprising an amidine ligand; and an activator. WO2005090418 discloses also a process for the copolymerisation of ethylene, alpha olefin and one or more non conjugated dienes. In some embodiments of WO2005090418, high non-conjugated diene incorporations are observed but these do not coincide with capability to produce high molecular weight polymer or with high catalyst productivity. In other embodiments of WO2005090418, high catalyst productivity and capability to produce high molecular weight polymer are observed but these do not coincide with high incorporations of non-conjugated dienes (see comparative examples).

Surprisingly and advantageously it is observed that catalyst components with a cyclopentadienyl ring bearing a certain bulky group such as a tert-butyl substituent, unexpectedly show high affinity for non-conjugated diene comonomers whilst retaining capability to produce high molecular weight polymer and being highly productive.

The process according to the invention employs for instance the monomeric units of ethylene, propylene, 5-ethylidene-2-norbornene and/or 5-vinyl-2-norbornene and shows a high relative copolymerization rate for 5-vinyl-2-norbornene as well as 5-ethylidene-2-norbornene compared to ethylene. This results in improved diene monomer utilization during the polymerization process whilst providing EPDM polymers with increased level of incorporated 5-ethylidene-2-norbornene and/or 5-vinyl-2-norbornene.

Due to the higher fraction of dienes like 5-ethylidene-2-norbornene and/or 5-vinyl-2-norbornene non conjugated diolefin that is polymerized with only one of the double bonds, the polymer comprises increased numbers of double bonds originating from the 5-ethylidene-2-norbornene and/or 5-vinyl-2-norbornene available for curing. It is known that the double bonds originating from the 5-ethylidene-2-norbornene give a high curing speed; especially if a sulfur based curing system is used.

For these reasons, it is very desirable to use the polymer made with the process of the present invention for the production in peroxide curing processes, preferably for the production of hoses, cable and wire covering, profiles and thermoplastic vulcanizates.

A purpose of the invention is to provide new catalyst components that provide a favourable combination of high diene affinity and high molecular weight capability than the catalyst components in the known process embodied in WO2005090418.

Details of the Invention

This objective is achieved with a metal complex of the formula (1)

$$CyLMZ_p(A)_n \qquad (1),$$

wherein
M is a group 4 metal
Z is an anionic ligand,
p is number of 1 to 2, preferably 2,
Cy is a cyclopentadienyl-type ligand substituted with at least one aliphatic $C_3$-$C_{20}$ hydrocarbyl group, which is bonded to the cyclopentadienyl-type ligand, in particular to its cyclopentadienyl ring, via a secondary, a tertiary or quaternary carbon atom and,
L is an amidinate ligand of the formula (2)

(2)

wherein the amidine-containing ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom and
A is a neutral Lewis base ligand selected from the list consisting of ether, thioether, amine, tertiary phosphane, imine, nitrile and isonitrile, wherein the number of said metal ligands "n" is in the range of 0 to the amount that specifies the 18-electron rule.

M

In a preferred embodiment the metal M of group 4 is titanium (Ti), zirconium (Zr) or hafnium (Hf), most preferably titanium.

Cy

As used herein, the term cyclopentadienyl-type ligand is meant to broadly convey its conventional meaning, namely a substituted ligand having a five-membered carbon ring which is bonded to the metal via a π-type bonding usually in adopting $\eta^5$-coordination to the metal.

Thus, the term cyclopentadienyl-type includes cyclopentadienyl, indenyl and fluorenyl. The fact that one or more aromatic hydrogen atoms of the cyclopentadienyl-type structure may be replaced by one or more other residues allows numbers of substituents between 1 and 5 for the cyclopentadienyl ligand, 1 to 7 for the indenyl ligand and 1 to 9 for the fluorenyl ligand.

In the preferred case, the cyclopentadienyl-type ligand is substituted with one aliphatic $C_3$-$C_{20}$ hydrocarbyl substituent, in particular aliphatic $C_4$-$C_{20}$ hydrocarbyl substituent which is bonded to the cyclopentadienyl-type ligand, in particular to the cyclopentadienyl ring, via a secondary, a tertiary or quaternary carbon atom. The aliphatic $C_3$-$C_{20}$ hydrocarbyl substituent, may may be substituted by a substituent selected from the group consisting of Halogen, in particular F, Cl and Br and $C_6$-$C_{20}$-aryl, in particular phenyl, methylphenyl, trimethylphenyl, cyclohexylphenyl, napthyl, butylphenyl, butyldimethylphenyl.

Non-limiting examples of the $C_3$-$C_{20}$ hydrocarbyl substituent having a secondary, tertiary and/or quaternary carbon atoms are: iso-propyl, sec-butyl, tert-butyl, 3-pentyl, sec-pentyl, tert-pentyl, cyclopropyl, cyclobutyl, cyclopentyl, cyclohexyl, phenylcyclohexyl, methylcyclohexyl, cycloheptyl, cyclooctyl, cyclodecyl, cyclododecyl, isopropyldodecyl, adamantyl, norbornyl, tricyclo[5.2.1.0]decyl.

In a preferred embodiment the cyclopentadienyl ligand is monosubstituted by a tert-butyl group and in consequence Cy is tert-butylcyclopentadienyl, $^tBuCp$.

The cyclopentadienyl-type ligand may in addition to the aliphatic $C_3$-$C_{20}$ hydrocarbyl substituent, which is bonded to the cyclopentadienyl-type ligand via a secondary, a tertiary or quaternary carbon atom, comprise further substituents including halogen, in particular F, Cl and Br may be mentioned and furthermore other $C_1$-$C_{20}$ linear and branched alkyl radicals that are linked to the cyclopentadienyl ring by other C-atoms than via a secondary, a tertiary or quaternary carbon atom such as methyl, ethyl, propyl, butyl, pentyl, hexyl, heptyl, octyl, nonyl, and decyl, $C_1$-$C_{20}$ hydrocarbyl-substituted and unsubstituted aryl radicals including phenyl, methylphenyl, trimethylphenyl, cyclohexylphenyl, napthyl, butylphenyl, butyldimethylphenyl; $C_1$-$C_{20}$ substituted hydrocarbyl radicals including benzyl, N,N-dimethylaminobenzyl, N,N-dimethylaminomethyl, methoxymethyl, diphenyl-phosphinomethyl, fluorophenyl, trifluoromethylphenyl, fluoromethyl and cyanoethyl.

Z

In a preferred embodiment Z independently means a halogen atom, a $C_{1-10}$ alkyl group, a $C_{7-20}$ aralkyl group, a $C_{6-20}$ aryl group or a $C_{1-20}$ hydrocarbon-substituted amino group, and more preferably, a halogen atom and a $C_{1-10}$ alkyl group, most preferably Cl, F, Br, methyl, benzyl, methyltrimethylsilyl, phenyl, methoxyphenyl, dimethoxyphenyl, N,N-dimethylaminophenyl, bis-(N,N-dimethylamino)phenyl, fluorophenyl, difluorophenyl, trifluorophenyl, tetrafluorophenyl, perfluorophenyl, trialkylsilylphenyl, bis(trialkylsilyl)phenyl and tris(trialkylsilyl)phenyl. Most preferred are Cl or methyl. In case p is more than 1, means p=2, the given meanings for Z are independent. Preferably p=2 and both Z are identical.

L

A preferred embodiment of the invention relates to the metal complex of the formula (1) containing an amidine-containing ligand L of formula (2) wherein Sub1 is an aryl residue that may be substituted or unsubstituted. Typical examples for such a preferred amidinate-containing ligand are represented by formula 2 with Sub1 being a phenyl or substituted phenyl residue, preferable naphthyl, 2,6-dimethyl phenyl, 2,6-dichlorophenyl or 2,6-difluorophenyl.

A further embodiment of the invention relates to a metal complex of formula (1) having an L of the formula (2), wherein Sub1 is an alkyl residue. Typical examples for such a preferred Sub1 are linear, branched or cyclic alkyl residue with 1 to 20 carbon atoms, unsubstituted or substituted with halogen, amido, silyl or aryl radicals. Examples for such Sub1 are methyl, hexyl, cyclohexyl, iso-propyl, tert-butyl, benzyl, trifluoromethyl, 2,6-dimethyl benzyl, 2,6-difluoro benzyl and 2,6-difluorophenyl.

Another preferred embodiment of the present invention relates to a metal complex of the formula (1) having an L of the formula (2), wherein Sub2 is of the general formula —NR$^4$R$^5$ with R$^4$ and R$^5$ being individually selected from the group of aliphatic hydrocarbyl, halogenated aliphatic hydrocarbyl, aromatic hydrocarbyl and halogenated aromatic hydrocarbonyl residues. R$^4$ optionally forming a heterocyclic structure with R$^5$ or Sub1. Examples for Sub2 are dimethylamide, diisopropylamide and biscyclohexyl amide.

Most preferred examples of the amidinate-containing ligand represented by the formula (2) are based on protio-amidines of the formula (2a)

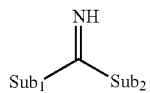

(2a)

Examples include N,N-dimethylacetimidamide, N,N-diisopropylacetimidamide, N,N-dicyclohexylacetimidamide, N-(2,6-dimethylphenyl)-N-ethylacetimidamide, N,N-dimethylisobutyrimidamide, N,N-diisopropylisobutyrimidamide, N,N-dicyclohexylisobutyrimidamide, N-(2,6-dimethylphenyl)-N-ethylisobutyrimidamide, N,N-dimethylcyclohexanecarboximidamide, N,N-diisopropylcyclohexanecarboximidamide, N,N-dicyclohexylcyclohexanecarboximidamide, N-(2,6-dimethylphenyl)-N-ethylcyclohexanecarboximidamide, N,N-dimethylpivalimidamide, N,N-diisopropylpivalimidamide, N,N-dicyclohexylpivalimidamide, N-(2,6-dimethylphenyl)-N-ethylpivalimidamide, 2,2,2-trifluoro-N,N-dimethylacetimidamide, 2,2,2-trifluoro-N,N-diisopropylacetimidamide, N,N-dicyclohexyl-2,2,2-trifluoroacetimidamide, N-(2,6-dimethylphenyl)-N-ethyl-2,2,2-trifluoroacetimidamide, 2-(phenyl)-N,N-dimethylacetimidamide, 2-(phenyl)-N,N-diisopropylacetimidamide, N,N-dicyclohexyl-2-(phenyl)acetimidamide, 2-(phenyl)-N-(2,6-dimethylphenyl)-N-ethylacetimidamide, 2-(2,6-dimethylphenyl)-N,N-dimethylacetimidamide, 2-(2,6-dimethylphenyl)-N,N-diisopropylacetimidamide, N,N-dicyclohexyl-2-(2,6-dimethylphenyl)acetimidamide, N,2-bis(2,6-dimethylphenyl)-N-ethylacetimidamide, 2-(2,6-difluorophenyl)-N,N-dimethylacetimidamide, 2-(2,6-difluorophenyl)-N,N-diisopropylacetimidamide, N,N-dicyclohexyl-2-(2,6-difluorophenyl)acetimidamide, 2-(2,6-difluorophenyl)-N-(2,6-dimethylphenyl)-N-ethylacetimidamide, N,N-dimethylbenzimidamide, N,N-diisopropylbenzimidamide, N,N-dicyclohexylbenzimidamide, N-(2,6-dimethylphenyl)-N-ethylbenzimidamide, N,N-dimethyl-1-naphthimidamide, N,N-diisopropyl-1-naphthimidamide, N,N-dicyclohexyl-1-naphthimidamide, N-(2,6-dimethylphenyl)-N-ethyl-1-naphthimidamide, N,N,2,6-tetra-methylbenzimidamide, N,N-diisopropyl-2,6-dimethylbenzimidamide, N,N-dicyclohexyl-2,6-dimethylbenzimidamide, N-(2,6-dimethylphenyl)-N-ethyl-2,6-di methyl benzimidamide, 2,6-difluoro-N,N-dimethylbenzimidamide, 2,6-difluoro-N,N-diisopropylbenzimidamide, N,N-dicyclohexyl-2,6-difluorobenzimidamide, N-(2,6-dimethylphenyl)-N-ethyl-2,6-difluorobenzimidamide, 2,6-dichloro-N,N-dimethylbenzimidamide, 2,6-dichloro-N,N-diisopropylbenzimidamide, 2,6-dichloro-N,N-dicyclohexylbenzimidamide, 2,6-dichloro-N-(2,6-dimethylphenyl)-N-ethylbenzimidamide. Preferred examples are 2,6-difluoro-N,N-piperidinylbenzamidine, 2,4-difluoro-N,N-diisopropylbenzimidamide (2,4-difluoro-N,N-diisopropylbenzamidine), 2,4,6-trifluoro-N,N-diisopropylbenzimidamide (2,4,6-trifluoro-N,N-diisopropylbenzamidine), 3,5-difluoro-N,N-diisopropylbenzimidamide (3,5-difluoro-N,N-diisopropylbenzamidine), pentafluoro-N,N-diisopropylbenzimidamide (pentafluoro-N,N-diisopropylbenzamidine), 2,6-difluoro-N,N-diisopropylbenzimidamide (2,6-difluoro-N,N-diisopropylbenzamidine) and N,N-diisopropylbenzimidamide (N,N-diisopropylbenzimidamide).

Another preferred embodiment of the present invention relates to a metal complex of the formula (1) having a ligand L of the formula 2b

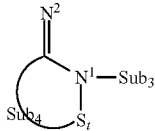

(2b)

wherein the amidine-containing ligand is covalently bonded to the metal M via the imine nitrogen atom $N^2$; S is a —$CH_2$— unit, and t is the integer number denoting the number of S and is in the range of 1-4, more preferably in the range of 1-2, most preferably is 1; Sub3 is an aliphatic or aromatic cyclic or linear substituent comprising a group 14 atom through which Sub3 is bonded to the amine nitrogen atom $N^1$;

Sub4 is an optionally substituted C2 unit in which the 2 carbon atoms may be $sp^2$ or $sp^3$ hybridized.

A preferred embodiment of the invention relates to a metal complex of formula 1 wherein Sub3 is an alkyl, alkenyl, alkynyl with 1 to 20 carbon atoms or aromatic residue with 6 to 20 carbon atoms, which are in each case unsubstituted or substituted with halogen, amido, silyl or aryl radicals. Examples for such Sub3 are methyl, n-propyl, i-propyl, tert-butyl, pentyl, cyclopentyl, hexyl, cyclohexyl, heptyl, cycloheptyl, octyl, cyclooctyl, cyclododecyl, octadecyl, adamantly, 1-butenyl, 2-butenyl and propenyl, unsubstituted phenyl or substituted phenyl residue, preferably phenyl, naphthyl, 2,6-dimethylphenyl, 2,6-dichlorophenyl or 2,6-difluorophenyl.

A preferred embodiment of the invention relates to a metal complex of formula 1 wherein L of the formula 2b) has the general formula 2c)

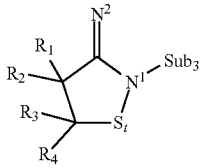

(2c)

wherein $R_1$-$R_4$ are the same or different and each represents a hydrogen atom, a halogen atom, an optionally substituted C1-10 alkyl group or an optionally substituted C1-10 alkoxy group, and S, t and Sub3 have the above mentioned meaning, or L of the formula 2b) has the general formula 2d)

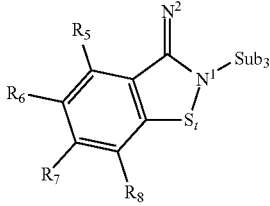

(2d)

wherein $R_5$-$R_8$ are the same or different and each represents a hydrogen atom, a halogen atom, an optionally substituted C1-10 alkyl group, an optionally substituted C1-10 alkoxy group, or the adjacent $R_5$-$R_8$ may be linked to form an aromatic ring optionally substituted, preferably unsubstituted, and S, t and Sub3 have the above mentioned meaning. Typical examples for preferred $R_5$-$R_8$ are hydrogen and fluorine.

In a preferred embodiment, in which L has the general form 2c) with $R_1$-$R_4$ each representing a hydrogen atom or 2d) with $R_5$-$R_8$ each representing a hydrogen atom or $R_5$ being a fluorine atom and with Sub3 being methyl, n-propyl, i-propyl, tert-butyl, pentyl, cyclopentyl, hexyl, cyclohexyl, heptyl, cycloheptyl, octyl, cyclooctyl, cyclododecyl, octadecyl, adamantly, 1-butenyl, 2-butenyl, propenyl, phenyl, naphthyl, 2,6-dimethylphenyl, 2,6-dichlorophenyl or 2,6-difluorophenyl, S means $CH_2$ and t is 1.

A

Preferred is a metal complex of the formula (1) wherein A is an ether, a thioether, a amine, a tertiary phosphane, an imine, a nitrile, an isonitrile, or a bi- or oligodentate donor.

If more than one ligand A is present they may have different meanings.

The number "n" of neutral ligands in the metal complex of formula (1) may range from 0 to the amount that satisfies the 18-electron rule, as known in the art. Preferably from 0 to 2. In the preferred embodiment the number "n" of neutral ligands A is 0 or 1.

Suitable ethers are diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers. Suitable thioethers are dimethyl sulfide, diethyl sulfide, thiophene, and tetrahydrothiophene. Suitable amines such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-lutidine, 2,6-di(t-butyl) pyridine, quinoline, and isoquinoline, preferably tertiary amines such as trialkylamines, pyridine, bipyridine, tetramethylethylenediamine (TMEDA), and (−)-sparteine). Suitable tertiary phosphanes are triphenylphoshine and trialkylphosphanes. Suitable of imines are ketimines, guanidines, iminoimidazolidines, phosphinimines and amidines. Suitable bidentate ligands are diimines, alkyl or aryldiphoshanes, dimethoxyethane. Suitable oligodentate ligands are triimines (such as tris(pyrazolyl)alkanes), cyclic multidentate ligands comprising heteroatoms of group 13-17, including crown ethers optionally having heteroatoms of group 13-17, azo-crown ethers optionally having heteroatoms of group 13-17, phospha-crown ethers optionally having heteroatoms of group 13-17, crown ethers having combinations of heteroatoms of group 15-16 optionally having heteroatoms of group 13-17 and crown ethers containing heteroatoms of group 14-17 or combinations thereof.

Suitable nitriles are those of the formula, $R^1C\equiv N$, where $R^1$ is individually selected from the group of aliphatic hydrocarbyl, halogenated aliphatic hydrocarbyl, aromatic hydrocarbyl and halogenated aromatic hydrocarbonyl residues. Preferred nitriles are acetonitrile, acrylonitrile, cyclohexanedintirile, benzonitrile, pentafluorbenzonitrile, 2,6-difluorobenzonitrile, 2,6-dichlorobenzonitrile, 2,6-dibromobenzonitrile, 4-fluoro-2-trifluoromethyl benzonitrile, 3-pyridinecarbonitrile Suitable isonitriles are those of the formula, $R^2N\equiv C$, where $R^1$ is individually selected from the group of aliphatic hydrocarbyl, halogenated aliphatic hydrocarbyl, aromatic hydrocarbyl and halogenated aromatic hydrocarbonyl residues. Preferred isonitriles are tert-butyl isocyanide ($^t$BuNC), ethyl isocyanoacetate, p-toluenesulfonylmethyl isocyanide and cyclohexyl isocyanide preferably tert-butyl isonitrile ($^t$BuNC).

A preferred neutral Lewis base ligand A means tetrahydrofuran (THF).

In a preferred embodiment the catalyst system according to the present invention contains a metal complex of formula (1), wherein
M is Ti,
Z is selected from the group consisting of chlorine and $C_1$-$C_4$-alkyl, preferably methyl,
p is 2
Cy is a tert-butylcyclopentadienyl ligand,
L means N,N-diisopropylbenzamidinate or 2,6-difluoro-N,N-diisopropylbenzamidinate or pentafluoro-N,N-diisopropylbenzamidinate
and
A means THF with n meaning 0 or 1. Preferably n=0
Process The invention further relates to a process for the manufacturing of a metal complex of formula (1) according to the present invention wherein a metal complex of the formula (3)

$$CyMZ_{p+1} \qquad (3)$$

is optionally reacted with a neutral Lewis base A to form the metal complex of the formula $CyMZ_{p+1}(A)_n$ wherein the radicals Cy, A, M, p and n have the above given meanings and Z means halogen, in particular Cl, Br, or F, and subsequently reacted with an amidine of the formula LH or its hydrohalogen acid salt LH.HZ wherein L has the above mentioned meaning and Z means halogen, in particular Cl, Br, or F.

The reaction with LH or its hydrohalogen acid salt LH.HZ is preferably carried out in a suitable solvent and preferably in the presence of suitable base.

Suitable bases include organic bases, inorganic bases, and organometallics. Typical examples for suitable bases are triethylamine and methylmagnesium bromide/chloride.

A suitable solvent is preferably an aromatic or aliphatic hydrocarbon solvent. The reaction is preferably carried out at ambient pressure, preferably at 0.9 bar to 1.1 bar, and a temperature in the range of 0 to 90° C. More preferably, in the range 20 to 60° C.

The molar ratio of LH or LH.HZ to $CyMZ_{p+1}(A)_n$ is preferably in the range of 0.8 to 1.5, most preferably the ratio is 0.95 to 1.050. The molar ratio of suitable base to LH, LH.HZ is preferably in the range of 1 to 5, more preferably the ratio is 2 to 4.

The metal complex of formula (1) wherein Z means a halogen atom may be isolated using techniques well known to those skilled in the art by filtration, to remove any inorganic or organic salt byproducts, followed by removal of volatiles under reduced pressure or by crystallization with subsequent removal of the mother liquor by filtration or by decantation. Optionally the crude mixture may be employed in polymerization reactions without further work-up or purification steps.

Techniques well-known to those skilled in the art are used to obtain further a metal complex of the formula 1 wherein Z means a C1-10 alkyl group, a C7-20 aralkyl group, a C6-20 aryl group from the metal complex of formula (1) wherein Z means a halogen atom by using suitable hydrocarbylating reagents for the salt metathesis reaction preferably in a suitable solvent. Preferably, Grignard reagents or organolithium reagents are employed as alkylating agents. The molar ratio of hydrocarbylating agent, in particular the alkylating agent to the metal complex of formula (1) is preferably in the range of 1.8 to 5.0, more preferably in the range 2.0-2.5. The alkylating agent is preferably methyl magnesium chloride or methyl lithium. This may be carried out at ambient pressure, preferably at 0.9 bar to 1.1 bar and a temperature in the range of 0 to 90° C. Preferably in the range 0 to 30° C.

Alternatively, a metal complex of the formula (1) wherein Z means a C1-10 alkyl group, a C7-20 aralkyl group, a C6-20 aryl group may be prepared by combining LH or LH.HZ with $CyMZ_{p+1}(A)_n$ wherein Z means a C1-10 alkyl group, a C7-20 aralkyl group, a C6-20 aryl group and A, p and n have the above mentioned meaning in a suitable solvent. Suitable solvents preferably are aromatic or aliphatic hydrocarbon solvents. This may be carried out at ambient pressure, preferably at 0.9 bar to 1.1 bar, preferably at temperatures in the range of 0 to 120° C. More preferably in the range 70 to 110° C.

The invention further provides a catalyst system comprising
a) a metal complex of the formula (1) according to the present invention and
b) an activator and
c) optionally a scavenger.

The preferred metal complex of compound a) is mentioned above. A scavenger c) is a compound that reacts with impurities present in the process of the invention, which are poisonous to the catalyst.

In a preferred embodiment of the present invention the scavenger c) as of the catalyst system is a hydrocarbyl of a metal or metalloid of group 1-13 or its reaction products with at least one sterically hindered compound containing a group 15 or 16 atom. Preferably, the group 15 or 16 atom of the sterically hindered compound bears a proton. Examples of these sterically hindered compounds are tert-butanol, iso-propanol, triphenylcarbinol, 2,6-di-tert-butylphenol, 4-methyl-2,6-di-tert-butylphenol, 4-ethyl-2,6-di-tert-butylphenol, 2,6-di-tert-butylanilin, 4-methyl-2,6-di-tert-butylanilin, 4-ethyl-2,6-di-tert-butylanilin, HMDS (hexamethyldisilazane), diisopropylamine, di-tert-butylamine, diphenylamine and the like. Some non-limiting examples of scavengers are butyllithium including its isomers, dihydrocarbylmagnesium, and hydrocarbylzinc and their reaction products with a sterically hindered compound or an acid, such as HF, HCl, HBr, Hl. Furthermore organoaluminium compounds (E) as defined below can be used as activator b), in particular hydrocarbylaluminoxanes like methylaluminoxane (MAO).

Activators of the component b) for single-site catalysts are fairly well known in the art. These activators often comprise a group 13 atom, such as boron or aluminium. Examples of these activators are described in *Chem. Rev.*, 2000, 100, 1391 by E. Y-X. Chen and T. J. Marks. A preferred activator b) is a borane (C1), a borate (C2, C3) or an organoaluminum compound (E) like alkylaluminoxane such as methyl aluminoxane (MAO). The activator for activation preferably is any boron compound of the following (C1) to (C3) and/or an organoaluminum compound (E).

The organoaluminum compound (E) may be employed as a scavenger and/or an activator.

(C1) A boron compound represented by the general formula $BQ_1Q_2Q_3$ (C2) A boron compound represented by the general formula $G(BQ_1Q_2Q_3Q_4)$ (C3) A boron compound represented by the general formula $(J-H)(BQ_1Q_2Q_3Q_4)$ $Q_1$ to $Q_3$ are a halogen atom, hydrocarbon group, halogenated hydrocarbon group, substituted silyl group, alkoxy group or di-substituted amino group, and they may be the same or different. $Q_1$ to $Q_3$ are preferably a halogen atom, hydrocarbon group having 1 to 20 carbon atoms, halogenated hydrocarbon group having 1 to 20 carbon atoms, substituted silyl group having 1 to 20 carbon atoms, alkoxy group having 1 to 20 carbon atoms or amino group having 2 to 20 carbon atoms, and more preferably, $Q_1$ to $Q_3$ are a halogen atom, hydrocarbon group having 1 to 20 carbon atoms, or halogenated hydrocarbon group having 1 to 20 carbon atoms. Further preferably, $Q_1$ to $Q_3$ are a fluorinated hydrocarbon group having 1 to 20 carbon atoms containing at least one fluorine atom, and particularly preferably, $Q_1$ to $Q_3$ are a fluorinated aryl group having 6 to 20 carbon atoms containing at least one fluorine atom. $Q_4$ has the same meaning as one of the radicals $Q_1$ to $Q_3$ and $Q_1$ to $Q_4$ may be the same or different. G is an inorganic or organic cation, J is a neutral Lewis base, and (J-H) is a Bronsted acid.

In the boron compound (C1) represented by the general formula $BQ_1Q_2Q_3$, B is a boron atom in the trivalent valence state, $Q_1$ to $Q_3$ have the above mentioned meanings and may be the same or different.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenyl-bis(pentafluoro-phenyl)borane and the like, and tris(pentafluorophenyl)borane is most preferable.

In the boron compound (C2) represented by the general formula $G(BQ_1Q_2Q_3Q_4)$, $G^+$ is an inorganic or organic cation, B is a boron atom in the trivalent valence state, and $Q_1$ to $Q_4$ are as defined for $Q_1$ to $Q_3$ in the above-mentioned (C1).

Specific examples of the inorganic cation G in a compound represented by the general formula $G(BQ_1Q_2Q_3Q_4)$ include a ferrocenium cation, alkyl-substituted ferrocenium cation, silver cation and the like, specific examples of the organic cation G thereof include a triphenylmethyl cation and the like. G is preferably a carbenium cation, and particularly preferably a triphenylmethyl cation.

Examples of (B $Q_1Q_2Q_3Q_4$) include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, teterakis(2,3,4-trifluorophenyl)borate, phenyltris(pentafluoro-phenyl) borate, tetrakis(3,5-bistrifluoromethylphenyl)borate and the like.

As specific combination of them, ferroceniumtetrakis(pentafluorophenyl)borate, 1,1'-dimethylferroceniumtetrakis(pentafluorophenyl)borate, silvertetrakis(pentafluorophenyl)borate, triphenylmethyltetrakis-(pentafluorophenyl)borate, triphenylmethyltetrakis(3,5-bistrifluoromethylphenyl)borate and the like are listed, and triphenylmethyltetrakis(pentafluorophenyl)borate is most preferable.

In the boron compound (C3) represented by the general formula $(J-H)^+(BQ_1Q_2Q_3Q_4)$, J is a neutral Lewis base, (J-H) is a Bronsted acid, B is a boron atom in the trivalent valence state, and $Q_1$ to $Q_4$ are as defined for $Q_1$ to $Q_4$ in the above-mentioned Lewis acid (C1).

Specific examples of the Bronsted acid $(J-H)^+$ in a compound represented by the general formula (J-H) $(BQ_1Q_2Q_3Q_4)$ include a trialkyl-substituted ammonium, N,N-dialkylanilinium, dialkylammonium, triaryl phosphonium and the like, and as the (B $Q_1Q_2Q_3Q_4$), the same compounds as described above are listed. As specific combination of them, there are listed triethylammoniumtetrakis(pentafluoro-phenyl)-borate, tripropylammoniumtetrakis(pentafluorophenyl)borate, tri(n-butyl)ammonium-tetrakis(pentafluorophenyl)borate, tri(n-butyl)ammoniumtetrakis(3,5-bistrifluoromethyl-phenyl)borate, N,N-dimethylaniliniumtetrakis(pentafluoro-phenyl)borate, N,N-diethylaniliniumtetrakis(penta-fluorophenyl)borate, N,N-2,4,6-pentamethylanilinium-tetrakis(pentafluorophenyl) borate, N,N-dimethylanilinium-tetrakis(3,5-bistrifluoromethyl-phenyl)borate, diisopropyl-ammoniumtetrakis(penta-fluorophenyl)borate, dicyclohexyl-ammoniumtetrakis-(pentafluorophenyl)borate, triphenylphosphoniumtetrakis(penta-fluorophenyl)borate, tri(methylphenyl)phosphoniumtetrakis(pentafluorophenyl)borate, tri(dimethylphenyl)-phosphonium-tetrakis(pentafluorophenyl)borate and the like, and tri(n-butyl)ammonium-tetrakis(pentafluorophenyl)borate or N,N-dimethylaniliniumtetrakis(pentafluoro-phenyl)borate is most preferable.

The molar ratio of metal complex:activating cocatalyst C1-C3 employed preferably ranges from 1:10 to 2:0, more preferably ranges from 1:5 to 1:0, and most preferably from 1:3 to 1:1.

The organoaluminum compound (E) is an aluminum compound having a carbon-aluminum bond, and one or more of aluminum compounds selected from the following (E1) to (E3) are preferable.

(E1) An organoaluminum compound represented by the general formula $T^1_a AlZ_{3-a}$ (E2) A cyclic aluminoxane having a structure represented by the general formula $\{-Al(T^2)-O-\}_b$ (E3) Linear aluminoxane having a structure represented by the general formula $T^3\{-Al(T^3)-O-\}_c AlT^3_2$ (wherein, each of $T^1$, $T^2$ and $T^3$ is hydrocarbon group, and all $T^1$, all $T^2$ and all $T^3$ may be the same or different respectively. Z represents a hydrogen atom or halogen atom, and all Z's may be the same or different. 'a' represents a number satisfying $0<a\leq 3$, 'b' is an integer of 2 or more, and 'c' is an integer of 1 or more.).

The hydrocarbon group in E1, E2 or E3 is preferably a hydrocarbon group having 1 to 8 carbon atoms, and more preferably an alkyl group.

Specific examples of the organoaluminum compound (E1) represented by the general formula $T^1_a AlZ_{3-a}$ include trialkylaluminums such as trimethylaluminum, triethyl-aluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth. A preferred activator-scavenger combination is $[CPh_3][B(C_6F_5)_4]$/MAO.

Specific examples of cyclic aluminoxane E2 having a structure represented by the general formula {—Al(T²)-O—}$_b$ and the linear aluminoxane E3 having a structure represented by the general formula T³{—Al(T³)—O-}$_c$AlT³$_2$ include alkyl groups such as a methyl group, ethyl group, n-propyl group, isopropyl group, n-butyl group, isobutyl group, n-pentyl group, neopentyl group and the like. b is an integer of 2 or more, c is an integer of 1 or more. Preferably, T² and T³ represent a methyl group or isobutyl group, and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which la trialkylaluminum (for example, trimethylaluminum and the like) is allowed to contact with a metal salt containing crystal water (for example, copper sulfate hydrate and the like) to produce aluminoxane.

The molar ratio of metal complex (1): scavenger c) employed preferably ranges from 0.1:1000 to 0.1:10, more preferably ranges from 0.1:1000 to 0.1:300, and most preferably from 0.14:600 to 0.14:400.

Polymerization

The invention further provides a process for the polymerization of a polymer by polymerizing at least one olefinic monomer comprising contacting said monomer with a metal complex of formula (1).

The metal complex of the formula (1) may also be used as a supported catalyst which comprises a organometallic compound of formula (1), a supporting material and optionally the activator (b) and/or a scavenger (c).

A supporting material is defined as an inorganic or organic compound that does not dissolve in the inert hydrocarbon solvent in which the process of the invention is carried out. Suitable inorganic supports include silica, magnesium halides, such as $MgF_2$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

The preferred process for polymerization is generally concluded by consulting at least one olefinic monomer with the metal complex of the formula (1) or the catalyst system according to the present invention in the gas phase, in slurry, or in solution in an inert solvent preferable a hydrocarbon solvent. Suitable solvents are in the gas phase, in slurry, or in solution in an inert solvent preferable a hydrocarbon solvent. Suitable solvents are a $C_{5-12}$ hydrocarbon such as pentane, hexane, heptane, octane, isomers and mixtures thereof, cyclohexane, methylcyclohexane, pentamethyl heptane and hydrogenated naphtha. The process of the invention may be conducted at temperatures from 10 to 250° C., depending on the product being made.

Monomer Definition

An olefinic monomer is understood to be a molecule containing at least one polymerizable double bond.

Suitable olefinic monomers are $C_{2-20}$ olefins. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, and $C_{4-12}$ straight chained or cyclic hydrocarbyl radicals which are unsubstituted or substituted by a $C_{1-4}$ alkyl radical. Illustrative non-limiting examples of such a-olefins are propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-hepta-decene, 1-octadecene, 1-nonadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 9-methyl-1-decene, 11-methyl-1-dodecene and 12-ethyl-1-tetradecene. These a-olefins may be used in combination.

The monomer may also be a polyene comprising at least two double bonds. The double bonds may be conjugated or non-conjugated in chains, ring systems or combinations thereof, and they may be endocyclic and/or exocyclic and may have different amounts and types of substituents. This means that the polyene may comprise at least one aliphatic, alicyclic or aromatic group, or combinations thereof.

Suitable polyenes include aliphatic polyenes and alicyclic polyenes. More specifically, aliphatic polyenes can be mentioned, such as 1,4-hexadiene, 3-methyl-1,4-hexadiene, 4-methyl-1,4-hexadiene, 5-methyl-1,4-hexadiene, 4-ethyl-1,4-hexadiene, 1,5-hexadiene, 3-methyl-1,5-hexadiene, 3,3-dimethyl-1,4-hexadiene, 5-methyl-1,4-heptadiene, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methyl-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 1,6-octadiene, 6-methyl-1,6-octadiene, 7-methyl-1,6-octadiene, 6-ethyl-1,6-octadiene, 6-propyl-1,6-octadiene, 6-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nonadiene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicyclic polyenes may consist of at least one cyclic fragment. Examples of these alicyclic polyenes are vinylcyclohexene, vinylnorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclohexane, 1,4-diallylcyclohexane, 1-allyl-5-vinylcycloocatane, 1,5-diallylcyclooctane, 1-allyl-4-isopropenylcyclohexane, 1-isopropenyl-4-vinylcyclohexane and 1-isopropenyl-3-vinylcyclopentane, and 1,4-cyclohexadiene. Preferred polyenes are polyenes having at least one endocyclic double bond and optionally at least one exocyclic double bond, such as 5-methylene-2-norbornene and 5-ethylidene-2-norbornene, 5-vinylnorbornene, and 2,5-norbornadiene, dicyclopentadiene and vinylcyclohexene.

Examples of aromatic polyenes are divinylbenzene (including its isomers), trivinyl-benzene (including its isomers) and vinylisopropenylbenzene (including its isomers).

All of the above-mentioned monomers may be further substituted with at least one group comprising a heteroatom of group 13-17, or combinations thereof.

Homopolymers, copolymers and copolymers on the basis of 3 or more of the above-mentioned olefinic monomers and also blends thereof can be prepared with the process of the present invention.

In a preferred embodiment copolymers on the basis of ethylene, at least one $C_{3-12}$ alpha olefin, preferably propylene and at least one non-conjugated diene, preferably a diene selected from the group consisting of 5-methylene-2-norbornene 5-ethylidene-2-norbornene, 5-vinylnorbornene, 2,5-norbornadiene, dicyclopentadiene (DCPD) and vinylcyclohexene, preferably from the group consisting of 5-ethylidene-2-norbornene and 5-vinylnorbornene are made with metal complex of the present invention.

The invention further relates to polymers obtainable with the metal complex of the present invention or the catalyst system of the present invention. Below, the invention will be elucidated on the basis of the following examples and comparative experiments, without being limited thereto.

EXAMPLES

Test methods.
Size Exclusion Chromatography with IR detector (SEC-IR)
Equipment: Freeslate Rapid GPC system with single detection (Infrared detector IR4 Standalone by Polymer Char)
Columns: PLGel Mixed-B 10 μm (×3 300×7.5 mm columns)
Calibration: Calibration with linear polystyrene (PS) standards (molecular weight ca. 30-3000 kg/mol)
Temperature: 160° C.
Flow: 1.5 ml/min
Injection volume: 125 μl
Solvent/eluent: Distilled 1,2,4-trichlorobenzene with 0.4 g/l of BHT stabilizer
Sample preparation: Dissolving for 2 hours at approx. 160° C.
Filtration through 2 and 0.5 micron sintered glass filter
Sample concentration 1.5 mg/ml
NMR ($^1$H, 300 MHz, $^{13}$C 75.4 MHz, $^{19}$F 282 MHz) spectra were measured on a Bruker Avance 300 spectrometer.

Fourier transformation infrared spectroscopy (FT-IR), was used to determine the composition of the copolymers according to the method that is known in the art. The FT-IR measurement gives the composition of the various monomers in weight percent relative to the total composition.

Composition was determined using mid-range FT-IR spectroscopy (in the cases of Tables 1 and 2 using polymer samples deposited on gold-coated silicon wafers).

Intrinsic Viscosity (IV) (Tables 3-6) was measured at 135° C. in decahydronaphthalene as solvent (Ubbelohde). IV (Tables 1-2) is calculated from the Mw value (SEC-IR) with reference to a calibration line correlating Mw (SEC-IR 160° C.) and IV (Ubbelohde 135° C.).

Part I: Synthesis of Ligands and Compounds
General.

All manipulations were carried out using standard Schlenk line or dry-box techniques under an atmosphere of argon or dinitrogen. Solvents were degassed by sparging with dinitrogen and dried by passing through a column of the appropriate drying agent. Toluene was refluxed over sodium and distilled. Deuterated solvents were dried over potassium ($C_6D_6$) or $P_2O_5$ (CDCl$_3$ and CD$_2$Cl$_2$), distilled under reduced pressure and stored under dinitrogen in Teflon valve ampoules. NMR samples were prepared under dinitrogen in 5 mm Wilmad 507-PP tubes fitted with J. Young Teflon valves. $^1$H and $^{13}$C-{$^1$H} spectra were recorded at ambient temperature and referenced internally to residual protiosolvent ($^1$H) or solvent ($^{13}$C) resonances, and are reported relative to tetramethylsilane (d=0 ppm). Chemical shifts are quoted in δ (ppm) and coupling constants in Hz.

Synthesis of Ligands and Literature Compounds
Ligand A (2-(phenyl)-2,3-dihydro-isoindol-1-ylideneamine)

A Schlenk tube was charged with aniline (5.000 g, 53.69 mmol) dissolved in p-cymene (50 mL) and 2-(bromomethyl)benzonitrile (10.526 g, 53.69 mmol) under inert conditions. This was left stirring at 150° C. for 16 hours. The p-cymene was removed from the resulting white powder by filtration. The powder was washed with 3×~50 mL toluene, and then with n-hexanes (3×50 mL), using a filter cannula, and remaining n-hexane was removed in vacuo, yielding 14.33 g of the hydrobromide salt of the ligand (92.3%). $^1$H NMR (300 MHz, DMSO-d$^6$, R.T.); δ 10.20 (s, 1H, NH), 9.20 (s, 1H, NH), 8.46-7.58 (m, 9H, Ar—H), 5.35 (s, 2H, CH$_2$).

The neutral protio ligand A was obtained by neutralization of a diethylether solution the hydrobromide salt using 4 M NaOH (aq)), removal of the aqueous phase and evaporation of the volatiles under reduced pressure.

Ligand B (HNC(C$_6$F$_5$)($^i$Pr$_2$N))

AlCl$_3$ (1.07 g, 8.00 mmol) was placed in a microwave vial, and pentafluorobenzonitrile (1.00 mL, 8.00 mmol) was added. The vial was capped and put in an oil bath that was preheated to 110° C. When a uniform melt formed, diisopropylamine (1.35 mL, 9.60 mmol) was added. The reaction mixture was stirred for 3 hours, allowed to cool down to rt and quenched by addition of icewater (4 mL). The reaction mixture was partitioned between HCl solution (1 M, aqueous 20 mL) and EtOAc (20 mL). The organic phase was extracted with HCl solution (1 M, aqueous 20 mL), and the combined aqueous fractions were basified (NaOH, 4 M, aqueous) and extracted with EtOAc (3×20 mL). The combined organic fractions were then dried (Mg$_2$SO$_4$), filtered and concentrated in vacuo to yield the product (1.425 g, 60%) as brownish crystals. Subsequent sublimation at 65° C./0.6 mbar yielded colourless crystals (1.35 g, 90%). The overall yield was 54%.

$^1$H-NMR (300 MHz, CDCl$_3$) δ: 6.33 (1H, br. s., NH); 4.0-3.2 (2H, m., (CH$_3$)$_2$CH); 1.9-0.9 (12H, m., (CH$_3$)$_2$CH,). $^{19}$F-NMR (282 MHz, CDCl$_3$) δ: −142.63 (2F, m., ortho-C$_6$F$_5$); −154.65 (1F, m., para-C$_6$F$_5$); −160.75 (2F, m., meta-C$_6$F$_5$).

Ligand C (HNC(2,6-C$_6$H$_3$F$_2$)(NC$_5$H$_{10}$))

To a piperidine (5 mL, 50.6 mmol) solution in toluene (20 mL) was added MeMgCl (3.0 M in THF, 16.9 mL, 50.6 mmol). The solution was heated to 50° C., for two hours before allowing to cool to room temperature and transferring using a cannula to a solution of 2,6-difluorobenzonitrile (7.03 g, 50.6 mmol) in toluene (20 mL). The solution was stirred for 16 h at room temperature after which time the reaction was quenched by addition of water (1 mL). After stirring for an hour, anhydrous sodium sulfate was added and the solution was then filtered to remove salts. The clear solution was then washed with brine (2×40 mL) before removal of the volatiles under reduced pressure to yield a viscous yellow oil. This was then diluted with another portion of hexanes (15 mL) and placed at −20° C. for two days resulting in crystallization of the desired product. Yield=8.7 g (77%). $^1$H NMR (300 MHz) (CDCl$_3$) δ (ppm): 7.24 (m, 1 H, Ar); 6.86 (m, 2 H, Ar); 6.06 (m, 1 H, NH), 3.33

(br m, 4 H, NCH$_2$), 1.53 (br m, 6 H, CH$_2$CH$_2$CH$_2$) ppm. $^{19}$F-NMR (282 MHz, CDCl$_3$) δ: −113.30 ppm.

Ligand D (2-(cyclooctyl)-2,3-dihydro-isoindol-1-ylideneamine)

2-(Bromomethyl)benzonitrile (3.00 g, 15.3 mmol) and cyclooctylamine (1.95 g, 15.3 mmol) were mixed without solvent at room temperature. The reaction was performed at room temperature for 5 min. The resulting dark gel was washed with diethylether (3×20 mL) to yield the product as a white solid (3.72 g, 11.5 mmol, 75%). The hydrobromide salt of the ligand was isolated as a powder which was characterized by $^1$H NMR (300 MHz) (CDCl$_3$) δ (ppm): 1.7 (m, 15H); 4.7 (s, 2H); 5 (s, 1H); 7.6 (m, 4H) and $^{13}$C NMR (75 MHz) (CDCl$_3$) δ (ppm): 24.2; 27.4; 31.3; 52.3; 56.9; 126.7; 129.4; 160.8.

The neutral protio ligand D was obtained by neutralization of a diethylether solution the hydrobromide salt using 4 M NaOH (aq).

Ligand E (HNC(Ph)($^i$Pr$_2$N)) was prepared as described in WO 2005/090418.

Ligand F (HNC(3,5-C$_6$H$_3$F$_2$)($^i$Pr$_2$N))

Synthesized according to the procedure described for Ligand B in a yield of 704 mg (58%). $^1$H-NMR (300 MHz, CDCl$_3$) δ: 6.84-6.73 (3H, m, ArH); 5.95 (1H, br. s., NH); 3.57 (2H, septet., J=6.8, (CH$_3$)$_2$CH); 1.32 (12H, d, J=6.8, (CH$_3$)$_2$CH). $^{13}$C-NMR (75 MHz, CDCl$_3$) δ: 165.52 (iPr$_2$N C=NH); 163.36 (d., J=250.4, meta-C$_6$H$_3$F$_2$); 163.20 (d., J=250.4, meta-C$_6$H$_3$F$_2$); 144.34 (t., J=8.5, ipso-C$_6$H$_3$F$_2$); 109.55 (dd, J=8.3, 17.3, ortho-C$_6$H$_3$F$_2$); 103.99 (t., J=25.2, para-C$_6$H$_3$F$_2$); 48,85 (CH$_3$)$_2$CH), 21.10 (CH$_3$)$_2$CH). $^{19}$F-NMR (282 MHz, CDCl$_3$) δ: −108.99 (2F, s., meta-C$_6$H$_3$F$_2$).

Ligand G (2-(cyclohexyl)-2,3-dihydro-isoindol-1-ylideneamine)

2-(Bromomethyl)benzonitrile (4.90 g, 25.0 mmol) was dissolved in toluene (10 mL) and cyclohexylamine (2.48 g, 25.0 mmol), dissolved in toluene (10 mL), was added dropwise within 20 min. It was stirred at 50° C. overnight. The solvent was evaporated to approx. 10 mL and diethylether (20 mL) was added. It was filtered off, washed with diethylether (2×20 mL) and dried under reduced pressure to yield the product as a white solid (6.71 g, 22.8 mmol, 91%).

The hydrobromide salt of the ligand was isolated as a powder which was characterized by $^1$H NMR (300 MHz) (CDCl$_3$) δ (ppm): 1.10-2.14 (10H, m); 4.67 (2H, s); 4.95 (1H, m); 7.51 (1H, d); 7.58-7.68 (2H, m); 9.05 (1H, d); 9.81 (1H, s); 10.25 (1H, s).

The neutral protio ligand G was obtained by neutralization of a dichloromethane solution the hydrobromide salt using 4 M NaOH (aq), removal of the aqueous phase and evaporation of the volatiles under reduced pressure.

Ligand H (HNC(2,4,6-C$_6$H$_2$F$_3$)($^i$Pr$_2$N))

Synthesized according to the procedure described for Ligand B in a yield of 795 mg (44%). $^1$H-NMR (300 MHz, CDCl$_3$) δ: 6.75-6.65 (2H, m, ArH); 6.15 (1H, br. s., NH); 3.94-3.22 (2H, m., (CH$_3$)$_2$CH); 1.95-0.75 (12H, m., (CH$_3$)$_2$CH,). $^{19}$F-NMR (282 MHz, CDCl$_3$) δ: −108.08 (1F, t., J=5.9, para-C$_6$F$_5$); −111.44 (2F, d., J=5.9, ortho-C$_6$F$_5$).

Ligand I (HNC(2,6-C$_6$H$_3$F$_2$)($^i$Pr$_2$N)) was prepared as described in WO 2005/090418.

Ligand J (HNC(2,4-C$_6$H$_4$F$_2$)($^i$Pr$_2$N))

Synthesized according to the procedure described for Ligand B in a yield of 780 mg (46%). $^1$H-NMR (300 MHz, CDCl$_3$) δ: 7.22 (1H, td., J=8.2, 6.4 ortho-ArH); 6.93-6.77 (2H, m., meta-ArH); 6.00 (1H, br. s., NH); 3.58 (2H, septet., J=6.8, (CH$_3$)$_2$CH); 1.32 (12H, d, J=6.8, (CH$_3$)$_2$CH). $^{13}$C-NMR (75 MHz, CDCl$_3$) δ: 162.97 (dd., J=250.1, 11.5, ortho-CF); 161.17 (iPr$_2$NC=NH); 158.44 (dd., J=250.2, 11.9, para-CF); 129.59 (dd., J=9.6, 5.5, ortho-CH); 125.33 (dd., J=18.4, 4.1, ipso-CH); 112.03 (dd, J=21.4, 3.7, CFCHCH); 104.58 (t, J=25.5, CFCHCF); 48.93 (CH$_3$)$_2$CH), 20.99 (CH$_3$)$_2$CH). $^{19}$F-NMR (282 MHz, CDCl$_3$) δ: −109.98 (d, J=7.7), −112.30 (d, J=7.6).

Ligand K (2-(2,6-difluorophenyl)-2,3-dihydro-isoindol-1-ylideneamine)

A Schlenk tube was charged with 2,6-difluoroaniline (1.000 g, 5.10 mmol) dissolved in p-cymene (5 mL) and 2-(bromomethyl)benzonitrile (0.549 g, 5.10 mmol) under inert conditions and heated at 150° C. for 16 hours. The resulting powder was washed with toluene (3×5 mL), and then with n-hexane (3×5 mL), and dried in vacuo yielding 1.58 g of the hydrobromide salt of the ligand (95.3%).

$^1$H NMR (300 MHz, DMSO-d$^6$, R.T.); δ 10.78 (s, 1H, NH), 9.96 (s, 1H, NH), 8.51-7.50 (7H, Ar—H), 7.80, 5.33 (s, 2H, CH$_2$). $^{19}$F NMR (282 MHz, DMSO-d$^6$, R.T.); δ −118.05.

The neutral protio ligand K was obtained by neutralization of a dichloromethane solution the hydrobromide salt using 4 M NaOH (aq)), removal of the aqueous phase and evaporation of the volatiles under reduced pressure.

Compound P Cp*TiCl$_3$ was bought from Boulder Scientific Company and used as received.

Compound Q $^t$BuCpTiCl$_3$ was prepared as described in Macromolecules 2000, 33, 2796-2800.

Compound T (CpTiCl$_2$(NC(Ph)($^i$Pr$_2$N)) was prepared as described for compound 5 in WO 2005/090418.

Compound U Me$_5$CpTiCl$_2$(NC(Ph)($^i$Pr$_2$N)) was prepared as described for compound 6 in WO 2005/090418

Compound UM Me$_5$CpTiMe$_2$(NC(Ph)($^i$Pr$_2$N))

To a stirring toluene (15 mL) solution of Cp*Ti{NC(Ph)N$^i$Pr$_2$}Cl$_2$ (Compound B) (1.00 g, 2.20 mmol) was added dropwise MeLi (2.80 mL, 1.6 M in Et$_2$O, 4.40 mmol) and the resulting solution was stirred for 16 h. The volatiles were then removed in vacuo and the yellow solid was then extracted into n-hexanes (50 mL). Concentration of the solution to ca. 15 mL and subsequent storage at −30° C. for 24 h resulted in crystallisation of the desired product as large yellow crystals which were isolated and dried in vacuo. Yield=0.37 g (40%). The product was characterized by $^1$H-NMR and $^{13}$C-NMR. Cp* means η$^5$—C$_5$Me$_5$.

Compound V Me$_5$CpTiCl$_2$(NC(2,6-C$_6$H$_3$F$_2$)($^i$Pr$_2$N)) was prepared as described for compound 10 in WO 2005/090418

Compound VM Me$_5$CpTiMe$_2$(NC(2,6-C$_6$H$_3$F$_2$)($^i$Pr$_2$N)) was prepared as described for compound 10M in WO 2005/090418

Compound W ($^n$BuCp)TiCl$_2$(NC(2,6-C$_6$H$_3$F$_2$)($^i$Pr$_2$N)) was prepared as described for compound 15 in WO 2005/090418

Compound X Me$_5$CpTiCl$_2$(NC(C$_{13}$FH$_9$N)

To a solid mixture of (2-(2,6-difluorophenyl)-2,3-dihydro-isoindol-1-ylideneamine) (Ligand K) (4.50 g, 18.4 mmol) and Cp*TiCl$_3$ (5.33 g, 18.4 mmol) was added toluene (100 mL) and triethylamine (11.3 mL, 46.1 mmol). The solution was stirred for two days at room temperature. The volatiles were removed under reduced pressure before the resulting orange solid was extracted into toluene (2×250 mL). Following filtration, the solutions were concentrated to 100-120 mL and stored for two days at −35° C. The yellow crystalline solid was collected by filtration and washed carefully with hexanes (3×15 mL). Yield=4.75 g (52%). $^1$H NMR (300 MHz, C$_6$H$_6$, R.T.); δ 8.03-8.00 (m, 1H, CHC(C=N)), 7.04-7.01 (m, 2H, Ar), 6.71-6.69 (m, 1H, Ar), 6.65-6.63 (m, 3H, Ar), 4.05 (s, 2H, NCH$_2$C), 1.98 (s, 15H, C$_5$Me$_5$) ppm. $^{13}$C NMR (75 MHz, C$_6$D$_6$, R.T.); δ 161.89-158.46 (dd, J=253.6, 4.7 Hz, CF(Ar)), 159.74 (NC), 141.35

(Ar), 133.93 (Ar), 131.59 (Ar), 129.75-129.49 (t, J=9.8 Hz, CFCH$\underline{\text{C}}$HCHCF(Ar)), 128.63 (Ar), 127.90 (Ar), 125.31 (Ar), 122.96 ($\underline{\text{C}}_5$Me$_5$), 116.43 (t (very weak), N=CN$\underline{\text{C}}$CF), 112.40-112.09 (m, CF$\underline{\text{C}}$HCHCHCF), 53.83 (N$\underline{\text{C}}$H$_2$C), 13.02 (C$_5$$\underline{\text{Me}}_5$) ppm. $^{19}$F NMR (300 MHz, C$_6$H$_6$, R.T.); δ −115.4 ppm.

Inventive Complexes

Complex 1 ($^t$BuCp)TiCl$_2$(NC(Ph)($^i$Pr$_2$N))

To a solution of N,N-diisopropylbenzamidine (Ligand E) (0.500 g, 2.45 mmol) and $^t$BuCpTiCl$_3$ (0.674 g, 2.45 mmol) in toluene (30 mL), was added triethylamine (1.35 mL) and the mixture was stirred overnight at 50° C. The mixture was filtered and concentrated in vacuo, yielding the product as a bright yellow powder (0.77 g, 70.5%) $^1$H NMR (300 MHz, CDCl$_3$) δ: 7.50-7.16 (3H, ArH); 6.04 (2H, t, J=2.8 Hz, CpH); 5.77 (2H, t, J=2.8 Hz, CpH); 3.65 (2H, br. s., CH(CH$_3$)$_2$); 1.63 (6H, br. s., CH(CH$_3$)$_2$); 1.15 (9H, s, CpC(C$\underline{\text{H}}_3$)$_3$); 1.12 (6H, br. s., CH(CH$_3$)$_2$) ppm. $^{13}$C NMR (75 MHz, CDCl$_3$) δ: 166.3, 145.3, 138.6, 129.6, 129.2, 126.2, 114.8, 114.3, 53.1, 49.1, 33.3, 31.4, 20.84 ppm.

Complex 2 ($^t$BuCp)TiCl$_2$(NC(2,6-C$_6$H$_3$F$_2$)($^i$Pr$_2$N))

Prepared with 2,6-difluoro-N,N-diisopropylbenzimidamide (Ligand I) using the procedure described for Compound 1.

$^1$H-NMR (300 MHz, CDCl3) δ: 7.37 (1H, m, J=8.6, 6.4, p-ArH); 7.09-6.97 (2H, m, m-ArH); 6.29 (2H, t, J=2.7, CpH); 6.09 (2H, t, J=2.7, CpH); 3.75 (1H, sept, J=6.8 Hz, C$\underline{\text{H}}$(CH$_3$)$_2$); 3.63 (1H, sept, J=6.8 Hz, C$\underline{\text{H}}$(CH$_3$)$_2$); 1.68 (6H, d, J=6.8 Hz, CH(C$\underline{\text{H}}_3$)$_2$); 1.26 (9H, s, CpC(C$\underline{\text{H}}_3$)$_3$); 1.20 (6H, d, J=6.8 Hz, CH(C$\underline{\text{H}}_3$)$_2$) ppm. $^{13}$C-NMR (75 MHz, CDCl$_3$) δ: 158.3 (dd, $^1$J=250.1 Hz, $^3$J=7.3 Hz); 154.4; 146.3; 131.1 (t, $^3$J=9.5 Hz), 115.4 (t, $^2$J=23.3 Hz); 115.0; 114.45; 112.7-112.2 (m); 53.7; 49.3; 33.5; 31.3; 21.0; 20.8 ppm. $^{19}$F-NMR (282 MHz, CDCl$_3$) δ: −113.1 ppm.

Complex 2M ($^t$BuCp)TiMe$_2$(NC(2,6-C$_6$H$_3$F$_2$)($^i$Pr$_2$N))

Prepared with Compound 2 using the procedure described above for Compound UM.

$^1$H-NMR (300 MHz, CDCl$_3$) δ: 7.13 (1H, m, J=8.6 Hz, 6.4 Hz, p-Ar$\underline{\text{H}}$); 6.88-6.74 (2H, m, m-Ar$\underline{\text{H}}$); 5.82 (2H, t, J=2.7 Hz, Cp$\underline{\text{H}}$); 5.58 (2H, t, J=2.7 Hz, Cp$\underline{\text{H}}$); 3.70 (1H, sept, J=6.8 Hz, C$\underline{\text{H}}$(CH$_3$)$_2$); 3.62 (1H, sept, J=6.8 Hz, C$\underline{\text{H}}$(CH$_3$)$_2$); 1.61 (6H, d, J=6.8 Hz, CH(C$\underline{\text{H}}_3$)$_2$); 1.13 (9H, s, CpC(C$\underline{\text{H}}_3$)$_3$); 1.04 (6H, d, J=6.8 Hz, CH(C$\underline{\text{H}}_3$)$_2$); 0.10 (6H, s, Ti(C$\underline{\text{H}}_3$)$_2$) ppm. $^{13}$C-NMR (75 MHz, CDCl$_3$) δ: 158.2 (dd, J=247.9 Hz, 8.3 Hz); 149.1; 141.1; 128.8 (t, J=9.4 Hz); 118.6 (t, J=24.3 Hz); 111.9-111.3 (m); 110.4; 107.8; 52.2; 47.5; 46.5; 32.4; 31.50; 21.1; 20.5 ppm. $^{19}$F-NMR (282 MHz, CDCl$_3$) δ: −114.7 ppm.

Part II—In Situ Catalyst Formation

Catalysts were prepared in situ by employing a combinatorial approach using either C$_5$R$_5$TiCl$_3$ complexes (P and Q) and an equivalent quantity of one of the protio ligands A-K. For the in situ-generated complexes presented in Table 1, the protio ligand (A-K) was first deprotonated with one equivalent of MeMgCl (3.0M in THF) in toluene for thirty minutes at room temperature before a toluene solution of either P or Q (one molar equivalent) was added. Each combination of ligand A-K with metal precursor Q represents an invented catalyst component. The concentrations were adjusted such that the overall concentration of titanium in the final solution was 40 mM. The solutions were then employed in polymerization reactions (Part III).

Part III EPDM Co-Polymerizations Using In Situ-Generated Catalysts (Tables 1 and 2)

The polymerizations with the in situ-generated catalysts were carried out in 48 parallel pressure reactors (PPR48). The PPR reactor cells were fitted with a pre-weighed glass vial insert and a disposable stirring paddle. The reactors were sealed, tested with Nitrogen at 130 psi to ensure that leaks not higher than 0.1 psi min$^{-1}$ may occur. The reactor atmosphere was then purged three times with propene at 80 psi, and 3.9 mL of toluene was added (toluene was first purified by passing through MBraun SPS mixed bed columns), along with 200 mL of an ENB/MMAO-3A/BHT toluene solution with the following composition: ENB (Sigma Aldrich, used as received, 5% v/v) 34 mM (final reactor concentration), MMAO-3A (AKZO NOBEL) 50 mM and BHT (Sigma Aldrich, used as received) 25 mM. The liquid reactants were injected into each cell through a valve. The reactors were heated at 40° C. and the cells were pressurized with 50 psi of propene (Linde Gas, further purified through Selexorb and BASF catalysts for Oxygen and moisture removal) for 5 minutes with a stirring speed of the paddles of 800 rpm. After pressure stabilization, the reactors were heated at the polymerization temperature (90° C.) and the reactors were then left to equilibrate for 20 minutes. The reactors were then pressurized with ethene until a final pressure of 130 psi was reached. The pre-catalyst and activator (Trityl Tetrakis(pentafluorophenyl)borate (TBF20)) toluene solutions (4 mM) were injected into the cells preventing contact with a 50 μL nitrogen gap in the dispensation needle. The ratio of [B]:[Ti] was set at 2. The pre-catalyst loading was adjusted such that mass transport limitations were not encountered. The polymerization was run at constant temperature and ethene partial pressure for 5 minutes, then quenched with an oxygen/nitrogen mixture (2% Oxygen content v/v) at 50 psi (3.4 bar) overpressure. The reactors were cooled, vented and purged with N$_2$, in order to prevent the glove box pollution from the quenching gas. After purging with inert gas, the reactors were opened and the glass inserts were unloaded from the cells, transferred to the centrifuge/vacuum drying station (Genevac EZ-2 Plus) and the volatiles were removed under reduced pressure overnight. The polymer samples were then weighed on a Weighting Station unit and the polymer yields were recorded. The polymers were analysed for molecular weight (IV—calculated from Mw value (SEC-IR) with reference to a calibration line correlating Mw (SEC-IR 160° C.) and IV (Ubbelohde 135° C.), Mw/Mn and composition (FT-IR).

Part IV—Batch EPDM Co-Polymerizations (General Procedure) (Tables 3-6)

The batch co-polymerizations were carried out in a 2-liter batch autoclave equipped with a double intermig and baffles. The reaction temperature was set on 90+/−3° C. and controlled by a Lauda Thermostat. The feed streams (solvents and monomers) were purified by contacting with various adsorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back-pressure valve.

In an inert atmosphere of nitrogen, the reactor was filled with pentamethylheptanes (PMH) (950 mL), MAO-10T (Crompton, 10 wt % in toluene), BHT and, for the EPDM/EPDM high ENB experiments, 5-ethylidene-2-norbornene (ENB) and/or 5-vinyl-2-norbornene (VNB). The reactor was heated to 90° C., while stirring at 1350 rpm. The reactor was pressurized and conditioned under a determined ratio of ethylene, propylene and, for the EPDM/EPDM high ENB experiments, hydrogen (0.35 NL/h). After 15 minutes, the catalyst component was added into the reactor (0.1-0.8 μmol depending on catalyst productivity) and the catalyst vessel was rinsed with PMH (50 mL) subsequently. After 10 minutes of polymerisation, the monomer flow was stopped and the solution was carefully dumped in an Erlenmeyer flask of 2 L, containing a solution of Irganox-1076 in iso-propanol and dried over night at 100° C. under reduced pressure. The polymers were analysed for intrinsic viscosity (IV) and composition (FT-IR).

The experimental conditions and results are given in tables 3 to 6.

TABLE 1

| Example No. | Ligand | Metal Precursor | No. of polymerisations | No. of polymers analysed | Av. M-cont[1] (ppm Ti) | Av. C2[2] (wt. %) | Av ENB[2] (wt. %) | Av. IV[2] dL/g | Av. Mw/Mn[2] |
|---|---|---|---|---|---|---|---|---|---|
| 1 | A | Compound P | 6 | 6 | 8.1 | 33.6 | 2.2 | 3.9 | 2.1 |
| 2 | A | Compound Q | 6 | 6 | 9.8 | 33.7 | 8.9 | 3.0 | 2.1 |
| 3 | B | Compound P | 6 | 6 | 3.7 | 27.6 | 4.9 | 2.6 | 2.1 |
| 4 | B | Compound Q | 6 | 6 | 18.3 | 30.0 | 11.3 | 2.9 | 2.1 |
| 5 | C | Compound P | 6 | 6 | 3.3 | 32.8 | 6.8 | 4.2 | 2.3 |
| 6 | C | Compound Q | 6 | 6 | 18.6 | 32.6 | 10.3 | 4.1 | 2.1 |
| 7 | D | Compound P | 6 | 6 | 15.4 | 29.2 | 3.2 | 4.2 | 2.3 |
| 8 | D | Compound Q | 6 | 3 | 32.3 | 26.9 | 11.5 | 3.6 | 2.1 |
| 9 | E | Compound P | 6 | 6 | 2.9 | 35.1 | 8.8 | 3.9 | 2.1 |
| 10 | E | Compound Q | 6 | 5 | 7.5 | 34.4 | 13.5 | 2.8 | 2.1 |
| 11 | F | Compound P | 5 | 5 | 2.8 | 36.5 | 4.3 | 3.9 | 2.2 |
| 12 | F | Compound Q | 6 | 4 | 6.9 | 32.9 | 11.4 | 3.2 | 2.2 |
| 13 | G | Compound P | 6 | 3 | 25.9 | 27.9 | 7.5 | 4.2 | 2.3 |
| 14 | G | Compound Q | 6 | 6 | 19.7 | 28.8 | 14.0 | 3.2 | 2.1 |
| 15 | H | Compound P | 6 | 6 | 2.2 | 32.5 | 6.0 | 3.3 | 2.1 |
| 16 | H | Compound Q | 6 | 6 | 7.7 | 34.3 | 10.9 | 3.1 | 2.1 |
| 17 | I | Compound P | 5 | 6 | 1.9 | 32.6 | 6.3 | 3.5 | 2.2 |
| 18 | I | Compound Q | 6 | 6 | 4.6 | 33.4 | 10.4 | 3.1 | 2.1 |
| 19 | J | Compound P | 6 | 5 | 3.0 | 32.2 | 5.0 | 3.9 | 2.1 |
| 20 | J | Compound Q | 6 | 6 | 7.9 | 33.4 | 12.4 | 2.9 | 2.1 |
| 21 | K | Compound P | 5 | 5 | 4.9 | 24.0 | 3.4 | 3.6 | 2.1 |
| 22 | K | Compound Q | 5 | 5 | 8.0 | 34.0 | 5.4 | 3.2 | 2.1 |

[1] Average value determined from respective number of polymerizations.
[2] Average value determined from number of analysed polymers.

TABLE 2

| Example No. | Metal Precursor/ Isolated Catalyst | No. of polymerisations | No. of polymers analysed | Av. M-cont[1] (ppm Ti) | Av. C2[2] (wt. %) | Av ENB[2] (wt. %) | Av. IV[2] dL/g |
|---|---|---|---|---|---|---|---|
| 23 | X | 6 | 5 | 2.1 | 24.4 | 3.9 | 3.5 |
| 24 | 1 | 5 | 4 | 5.4 | 39.7 | 10.9 | 3.0 |
| 25 | 2 | 5 | 6 | 4.3 | 32.4 | 12.9 | 3.1 |
| 26 | 2M | 6 | 6 | 5.7 | 35.4 | 10.2 | 3.1 |

[1] Average value determined from respective number of polymerizations.
[2] Average value determined from number of analysed polymers.

TABLE 3

| Example No. | Complex | Exp. Type C3:C2 | Yield (gram) | M-cont (ppm Ti) | C2 (wt. %) | C3 (wt. %) | IV dL/g |
|---|---|---|---|---|---|---|---|
| 27 | 1 | 80:40 | 2.6 | 1.3 | 56.0 | 43.6 | 7.3 |
| 28 | 1 | 50:50 | 10.6 | 0.9 | 67.5 | 32.5 | 8.0 |
| 29 | 2 | 80:40 | 2.6 | 1.3 | 49.0 | 51.0 | 6.1 |
| 30 | 2 | 50:50 | 5.4 | 0.6 | 63.4 | 36.6 | 7.9 |
| 31 | 2M | 80:40 | 10.2 | 0.9 | 49.1 | 50.9 | 5.2 |
| 32 | 2M | 50:50 | 10.3 | 0.5 | 66.7 | 33.3 | 7.4 |

Table 3. 90° C., 7 bar, 10 min, MAO/BHT ([BHT] = 900 μmol/L; [Al] = 450 μmol/L. EPM 50/50: 250 NL/h $C_3$, 250 NL/h $C_2$, EPM 80/40: 400 NL/h $C_3$, 200 NL/h $C_2$,

TABLE 4

| Example No. | Complex | Exp. Type | Yield (gram) | M-cont (ppm Ti) | C2 (wt. %) | C3 (wt. %) | C9/ENB (wt. %) | VNB (wt. %) | IV dL/g |
|---|---|---|---|---|---|---|---|---|---|
| 33 | 1 | EPDM | 2.3 | 2.1 | 50.2 | 43.0 | 4.1 | 2.8 | 4.1 |
| 34 | 1 | EPDM high ENB | 2.3 | 2.1 | 47.5 | 38.3 | 14.3 | — | 3.4 |
| 35 | 2 | EPDM | 1.5 | 3.3 | 45.8 | 48.1 | 3.5 | 2.6 | nd |
| 36 | 2 | EPDM high ENB | 1.5 | 3.2 | 43.8 | 42.8 | 13.5 | — | nd |
| 37 | 2M | EPDM | 4.3 | 2.3 | 46.0 | 47.9 | 3.8 | 2.4 | 4.7 |
| 38 | 2M | EPDM high ENB | 4.7 | 2.0 | 42.9 | 45.8 | 11.3 | — | 3.5 |

Table 4. 90° C., 7 bar, 10 min, MAO/BHT ([BHT] = 900 μmol/L; [Al] = 450 μmol/L.
EPDM: 400 NL/h $C_3$, 200 NL/h $C_2$, 0.35 NL/h $H_2$, 0.7 mL VNB, 0.7 mL ENB. High ENB: 400 NL/h $C_3$, 200 NL/h $C_2$, 0.35 NL/h $H_2$, 2.8 mL ENB

TABLE 5

| Comparative Example No. | Compound | Exp. Type C3:C2 | Yield (gram) | M-cont (ppm Ti) | C2 (wt. %) | C3 (wt. %) | IV dL/g |
|---|---|---|---|---|---|---|---|
| 39 | T | 80:40 | 6.1 | 3.1 | 55.1 | 44.9 | 2.3 |
| 40 | T | 50:50 | 7.3 | 2.6 | 68.9 | 31.1 | 3.1 |
| 41 | UM | 80:40 | 12.5 | 0.2 | 52.6 | 47.4 | 7.5 |
| 42 | UM | 50:50 | 17.2 | 0.1 | 63.2 | 36.8 | 8.2 |
| 43 | VM | 80:40 | 13.8 | 0.2 | 47.7 | 52.3 | 5.5 |
| 44 | VM | 50:50 | 20.2 | 0.1 | 62.0 | 38.0 | 6.3 |

Table 5. 90° C., 7 bar, 10 min, MAO/BHT ([BHT] = 900 μmol/L; [Al] = 450 μmol/L. EPM 50/50: 250 NL/h $C_3$, 250 NL/h $C_2$, EPM 80/40: 400 NL/h $C_3$, 200 NL/h $C_2$,

TABLE 6

| Comparative Example No. | Compound | Exp. Type | Yield (gram) | M-cont (ppm Ti) | C2 (wt. %) | C3 (wt. %) | C9/ENB (wt. %) | VNB (wt. %) | IV dL/g |
|---|---|---|---|---|---|---|---|---|---|
| 45 | T | EPDM | 1.8 | 8.0 | 48.3 | 44.6 | 4.1 | 3.1 | nd |
| 46 | T | EPDM high ENB | 2.7 | 11 | 45.7 | 40.5 | 13.8 | — | 2.5 |
| 47 | U | EPDM | 7.5 | 0.6 | 45.1 | 53.1 | 1.1 | 0.7 | nd |
| 48 | V | EPDM | 8.5 | 0.6 | 42.0 | 56.2 | 1.1 | 0.7 | nd |
| 49 | VM | EPDM | 10.6 | 0.6 | 48.0 | 50.2 | 1.1 | 0.8 | 2.7 |
| 50 | VM | EPDM high ENB | 14.5 | 0.3 | 45.9 | 50.5 | 3.6 | — | nd |
| 51 | W | EPDM$^a$ | 3.8 | 3.8 | 42.0 | 53.3 | 2.7 | 2.0 | nd |
| 52 | W | EPDM$^{a,b}$ | 4.8 | 3.0 | 54.0 | 41.2 | 2.7 | 2.1 | nd |

Table 6. 90° C., 7 bar, 10 min, MAO/BHT ([BHT] = 900 μmol/L; [Al] = 450 μmol/L.
$^a$MAO/BHT ([BHT] = 1800 μmol/L; [Al] = 900 μmol/L. EPDM: 400 NL/h $C_3$, 200 NL/h $C_2$, 0.35 NL/h $H_2$
($^b$250 NL/h $C_3$, 250 NL/h $C_2$, 0.35 NL/h $H_2$), 0.7 mL VNB, 0.7 mL ENB. High ENB: 400 NL/h $C_3$, 200 NL/h $C_2$, 0.35 NL/h $H_2$, 2.8 mL ENB From Table 1, in all cases the invented catalysts derived from precursor Q, give higher ENB incorporations in combination with a given ligand (A-K) than observed for the corresponding catalysts derived from precursor P. The intrinsic viscosities (IV) are similar in most cases and higher for examples using the inventive combination of ligand B and precursor Q compared to ligand B with precursor P. The effect of the third monomer (ENB) can result in differences in molecular weight capability being less easily observed hence the additional comparison of ethylene-propylene copolymers (in the absence of a third monomer) in Tables 3 and 5. Table 2 demonstrates the similarity of polymer properties when the isolated catalysts (X, 1, 2 and 2M) are dosed compared to the corresponding in situ generated catalysts (P+K, Q+E, Q+I) shown in Table 1. Comparing the invented compounds (1, 2 and 2M) with the comparative compounds (T, UM and VM) we see from tables 3 and 5 that the intrinsic viscosity IV (a measure of the molecular weight of the polymer) is similar for the invented compounds and UM and VM. Compound T makes polymer with lower intrinsic viscosity, hence lower molecular weight and is less active than the invented compounds.

Comparing the invented compounds (1, 2 and 2M) with comparative compounds (U, V, VM and W), we see from tables 4 and 6 that the invented compounds give a superior incorporation of non-conjugated dienes (ENB) and (VNB) than the comparative compounds U, V, VM and W. The incorporation of ENB and VNB of the invented compounds is similar to compound T (but as described above compound T is less productive and is limited to producing lower molecular weight polymer).

Thus overall the invented compounds result in simultaneous capability to make high molecular weight polymer combined with high diene affinity.

The invention claimed is:
1. A metal complex of the formula (1)
   $CyLMZ_p(A)_n$ (1),
   wherein:
   M is a group 4 metal,
   Z is an anionic ligand,
   p is number of 1 to 2,
   Cy is tert-butylcyclopentadienyl,

L is an amidinate ligand of the formula (2)

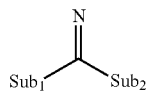

(2)

wherein the amidinate ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom, and
A is a neutral Lewis base ligand selected from the group consisting of ether, thioether, amine, tertiary phosphane, imine, nitrile and isonitrile, wherein the number "n" of the metal ligands is 0 to the amount that specifies the 18-electron rule.
2. The metal complex according to claim 1, wherein M is titanium.
3. The metal complex according to claim 1, wherein Z independently is a halide, a $C_{1-10}$ alkyl group, a $C_{7-20}$ aralkyl group, a $C_{6-20}$ aryl group, or a $C_{1-20}$ hydrocarbon-substituted amino group.
4. The metal complex according to claim 1, wherein:
   Sub1 is a phenyl or substituted phenyl residue, and
   Sub2 is an amino radical of the formula $—NR^4R^5$, with $R^4$ and $R^5$ being individually selected from the group consisting of aliphatic hydrocarbyl, halogenated aliphatic hydrocarbyl, aromatic hydrocarbyl, and halogenated aromatic hydrocarbonyl residues, whereby $R^4$ optionally forms a heterocyclic structure with $R^5$ or Sub1.

5. The metal complex according to claim 1, wherein:
M is Ti,
Z is selected from the group consisting of chloride and $C_1$-$C_4$-alkyl,
p is 2,
Cy is a tert-butylcyclopentadienyl,
L means N,N-diisopropylbenzamidinate, 2,6-difluoro-N,N-diisopropylbenzamidinate or pentafluoro-N,N-diisopropylbenzamidinate, and
A means THF with n meaning 0 or 1.

6. The metal complex of formula (1) according to claim 1, wherein the ligand L in formula (1) has formula 2b) wherein:

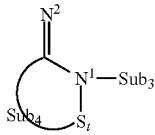

(2b)

the amidinate ligand is covalently bonded to the metal M via the imine nitrogen atom $N^2$;
S is a —$CH_2$— unit, and t is an integer of 1-4;
$Sub_3$ is an aliphatic or aromatic cyclic or linear substituent comprising a group 14 atom through which Sub3 is bonded to the amine nitrogen atom $N^1$; and
$Sub_4$ is an optionally substituted bidentate C2 unit in which the 2 carbon atoms may be $sp^2$ or $sp^3$ hybridized.

7. The metal complex according to claim 2, wherein:
Z is independently a halide, a $C_{1-10}$ alkyl group, a $C_{7-20}$ aralkyl group, a $C_{6-20}$ aryl group, or a $C_{1-20}$ hydrocarbon-substituted amino group;
$Sub_1$ is a phenyl or substituted phenyl residue; and
$Sub_2$ is an amino radical of the formula —$NR^4R^5$, with $R^4$ and $R^5$ being individually selected from the group consisting of aliphatic hydrocarbyl, halogenated aliphatic hydrocarbyl, aromatic hydrocarbyl, halogenated and aromatic hydrocarbonyl residues, whereby $R^4$ optionally forms a heterocyclic structure with $R^5$ or Sub1.

8. The metal complex according to claim 2, wherein:
Z is selected from the group consisting of chloride and $C_1$-$C_4$-alkyl,
p is 2,
Cy is a tert-butylcyclopentadienyl,
A is THF with n being 0 or 1, and
L is of the formula 2b) wherein:

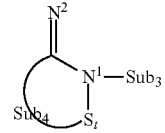

(2b)

the amidinate ligand is covalently bonded to the metal M via the imine nitrogen atom $N^2$;
S is a —$CH_2$— unit, and t is 1;
Sub3 is an aliphatic or aromatic cyclic or linear substituent comprising a group 14 atom through which Sub3 is bonded to the amine nitrogen atom $N^1$; and
Sub4 is an optionally substituted bidentate C2 unit in which the 2 carbon atoms are $sp^2$ or $sp^3$ hybridized.

* * * * *